(12) United States Patent
Quackenbush et al.

(10) Patent No.: US 7,279,903 B2
(45) Date of Patent: Oct. 9, 2007

(54) NON-METALLIC FLOW-THROUGH ELECTRODELESS CONDUCTIVITY SENSOR WITH LEAK AND TEMPERATURE DETECTION

(75) Inventors: John Kevin Quackenbush, Middleboro, MA (US); Michael M. Bower, Wareham, MA (US); Stephen B. Talutis, Milton, MA (US); Donald S. McKinlay, Wareham, MA (US); Daniel G. Tower, III, Wrentham, MA (US)

(73) Assignee: Invensys Systems, Inc., Foxboro, MA (US)

( * ) Notice: Subject to any disclaimer, the term of this patent is extended or adjusted under 35 U.S.C. 154(b) by 0 days.

(21) Appl. No.: 11/650,154

(22) Filed: Jan. 5, 2007

(65) Prior Publication Data
US 2007/0194792 A1 Aug. 23, 2007

Related U.S. Application Data

(63) Continuation-in-part of application No. 11/351,856, filed on Feb. 9, 2006.

(60) Provisional application No. 60/676,765, filed on May 2, 2005.

(51) Int. Cl.
G01N 27/06 (2006.01)
G01N 27/74 (2006.01)

(52) U.S. Cl. .................. 324/445; 324/439; 324/204

(58) Field of Classification Search .............. 324/445, 324/444, 546, 342, 204
See application file for complete search history.

(56) References Cited

U.S. PATENT DOCUMENTS 2,709,785 A 5/1955 Fielden
RE24,420 E 1/1958 Fielden (Continued)

FOREIGN PATENT DOCUMENTS

JP 2001147218 5/2001

OTHER PUBLICATIONS

C.W. Extrand, L. Monson; Gas Permeation Resistance of a Perfluoroalkoxy-Tetrafluoroethylene Copolymer; Journal of Applied Polymer Science; 2006; vol. 100, pp. 2122-2125.
Hydrofluoric Acid Monitors, CM-200/210; HORIBA, Bulletin: HRE-1889C, (pgs. 2).

Primary Examiner—Anjan K. Deb
(74) Attorney, Agent, or Firm—Sampson & Associates, P.C.

(57) ABSTRACT

A non metallic flow through electrodeless conductivity sensor is provided with a conduit having primary and secondary process fluid flow paths to form a fluid loop. At least one drive and one sense toroid surround the conduit on the fluid loop. Voltage supplied to the drive toroid induces a current in the sense toroid via the fluid loop to eliminate any need for metallic electrodes in contact with the process fluid. At least one additional drive and/or sense toroid is disposed on the fluid loop to enhance induction. Optionally one or more sense coils are disposed about the conduit outside of the fluid loop to cancel out stray electrical noise. An optional conductor disposed along the conduit detects any fluid leakage through changes in resistance thereof. A temperature detector is supported within an electrically non-conductive holder extending into the fluid flow path, so that the detector is free from physical contact with the fluid. An optional enclosure is provided with ports to enable a user to purge any gas permeating the conduit walls.

34 Claims, 17 Drawing Sheets

U.S. PATENT DOCUMENTS

| | | | |
|---|---|---|---|
| 3,292,077 A | 12/1966 | Sloughter | |
| 3,396,331 A | 8/1968 | Sperry, III | |
| 3,404,335 A | 10/1968 | Kidder | |
| 3,404,336 A | 10/1968 | Rosenthal | |
| 3,417,329 A | 12/1968 | Landis et al. | |
| 3,566,841 A | 3/1971 | Gerrish et al. | |
| 3,806,798 A | 4/1974 | Gross | |
| 3,867,688 A | 2/1975 | Koski | |
| 3,989,009 A | 11/1976 | Robar et al. | |
| 3,993,945 A | 11/1976 | Warmoth et al. | |
| 4,010,715 A | 3/1977 | Robar et al. | |
| 4,138,639 A | 2/1979 | Hutchins | |
| 4,220,920 A | 9/1980 | Gross | |
| 4,491,798 A | 1/1985 | Palmer et al. | |
| 4,740,755 A * | 4/1988 | Ogawa | 324/445 |
| 4,751,466 A | 6/1988 | Colvin et al. | |
| 4,825,168 A | 4/1989 | Ogawa et al. | |
| 5,003,267 A | 3/1991 | Coleman | |
| 5,025,220 A | 6/1991 | Colvin et al. | |
| 5,089,781 A | 2/1992 | Arichika et al. | |
| 5,157,332 A | 10/1992 | Reese | |
| 5,252,925 A | 10/1993 | Matsumoto et al. | |
| 5,268,642 A | 12/1993 | Uchidomi | |
| 5,341,102 A | 8/1994 | Akiyama et al. | |
| 5,510,716 A | 4/1996 | Buffaloe, IV et al. | |
| 5,510,717 A | 4/1996 | Buffaloe, IV et al. | |
| 5,570,026 A | 10/1996 | Buffaloe, IV et al. | |
| 5,612,622 A | 3/1997 | Goldman et al. | |
| 5,631,552 A | 5/1997 | Ogawa et al. | |
| 5,659,251 A | 8/1997 | Wakamatsu | |
| 5,680,051 A | 10/1997 | Wakamatsu | |
| 5,793,214 A | 8/1998 | Wakamatsu | |
| 5,900,726 A | 5/1999 | Brugger et al. | |
| 5,959,455 A | 9/1999 | Brown | |
| 6,075,367 A | 6/2000 | Brugger | |
| 6,122,956 A | 9/2000 | Klausner et al. | |
| 6,414,493 B1 | 7/2002 | Rezvani | |
| 6,452,371 B1 | 9/2002 | Brugger | |
| 6,489,785 B2 | 12/2002 | McAllister | |
| 6,653,841 B1 | 11/2003 | Koerdt et al. | |
| 7,078,909 B2 * | 7/2006 | Feng et al. | 324/439 |
| 2004/0012395 A1 | 1/2004 | Salamitou | |
| 2004/0249336 A1* | 12/2004 | Faries et al. | 604/28 |

* cited by examiner

NON-METALLIC FLOW-THROUGH ELECTRODELESS CONDUCTIVITY SENSOR WITH LEAK AND TEMPERATURE DETECTION

RELATED APPLICATION

This application is a continuation-in-part of U.S. patent application Ser. No. 11/351,856, entitled NON-METALLIC FLOW-THROUGH ELECTRODELESS CONDUCTIVITY SENSOR AND LEAK DETECTOR, filed on Feb. 9, 2006; which claims priority to U.S. Provisional Patent Application No. 60/676,765 entitled NON-METALLIC FLOW THROUGH ELECTRODELESS CONDUCTIVITY SENSOR, filed on May 2, 2005.

1. TECHNICAL FIELD

This invention relates to conductivity sensors and more particularly to electrodeless conductivity sensors configured to detect the conductivity of process fluid flowing through a conduit.

2. BACKGROUND INFORMATION

Throughout this application, various publications, patents and published patent applications are referred to by an identifying citation. The disclosures of the publications, patents and published patent applications referenced in this application are hereby incorporated by reference into the present disclosure.

Conductivity measurements of a chemical solution may be made by applying a voltage across a pair of electrodes and immersing them in the solution. The electric current passing through the system is proportional to the conductivity of the solution. This technique, however, is not optimal if the solution to be measured is chemically incompatible with the metallic electrodes, e.g., resulting in chemical attack or contamination of the solution and/or electrodes.

Another approach involves an electrodeless toroidal conductivity measurement. In this approach, an electric transformer is effectively created through the use of driver and sensor toroidal coils surrounding a 'core' formed at least partially by the solution under test. The toroids are typically disposed within an electrically insulative, magnetically transparent housing having a fluid flow path which passes axially therethrough. The driver is supplied with a voltage which induces an electromagnetic field in the solution passing through the flow path, which then induces a current in the sense coil. The induced current is proportional to the conductivity of the solution being measured.

An example of such a toroidal conductivity sensor is disclosed in Reese, U.S. Pat. No. 5,157,332. A commercial example of a similar sensor is known as the 871EC™ invasive conductivity sensor available from Invensys Systems, Inc. (Foxboro, Mass.). As shown in FIG. 1, a section of such an electrodeless conductivity sensor 20 includes toroidal coils 11, 12, 13 encased in a housing 21, which may be immersed in the fluid to be measured. The housing 21 defines a central bore 19 which allows fluid to pass axially through the toroids 11, 12, 13, without contacting them. The induction loop of the 'core' is completed by the process solution within which the sensor is immersed.

Where a fluid to be measured is flowing through a conduit, it may not be possible or desirable to immerse a sensor in the fluid. In this event, driver and sensor toroidal coils may surround a pipe carrying the liquid. A commercial example of such a sensor is known as the 871FT™ (Invensys Systems, Inc.). However, in order for induction to occur, an electrical loop must be completed outside the coils, typically by clamping a metallic strap to metallic portions of the pipe upstream and downstream of the toroids. A drawback of this approach, however, is that metallic pipe portions cannot be used when the process fluid attacks or is otherwise incompatible with metals.

Alternatively, the induction loop may be completed by the fluid itself, by providing a secondary flow path that bypasses one or more of the toroids. An example of such a fluid loop is disclosed in U.S. Pat. No. 2,709,785 to Fielden. A drawback of this approach is that the limited cross section, relatively long length and high resistance of the fluid itself, adds a net resistance to the induced current which tends to adversely affect the sensitivity of conductivity measurement. Approaches intended to enhance the sensitivity of conductivity sensors include that disclosed by Ogawa, in U.S. Pat. No. 4,740,755. Ogawa discloses toroids on a fluid loop with dimensions calculated to "provide a low value for the ratio of the length of fluid flow loop . . . to the cross sectional area of the flow path, which in turn provides good sensitivity." (Ogawa col. 2 lines 42-47). A drawback to this approach is that Ogawa's toroids are taught to be coplanar and physically separated in order to reduce leakage coupling between the transformers. (Ogawa at col. 1, lines 34-38, col. 2 lines 47-52, col. 4, lines 49-55).

The aforementioned corrosion and contamination issues also make temperature detection problematic for applications involving a metallically incompatible process fluids. This incompatibility militates against the conventional placement of metallic temperature detectors within the fluid flow path. One approach intended to avoid this problem is to place the temperature detector on the outside wall of the fluid flow conduit and to thus rely on thermal conduction through the conduit wall to obtain temperature data. However, conduits containing corrosive fluids are often fabricated from polymers such as PFA (perfluoroalkoxy polymer resin), PTFE (polytetrafluoroethylene), polyvinyl chloride (PVC), or various combinations thereof, such as perfluoroalkoxy-polytetrafluoroethylene co-polymer. The relatively poor thermal conductivity of these materials tends to adversely affect the accuracy and response time provided by such external temperature detection approaches.

A need therefore exists for a system of measuring the temperature of a process fluid flowing through a conduit, which addresses one or more of the abovementioned drawbacks.

SUMMARY

In accordance with one aspect of the invention, an electrodeless conductivity sensor includes an electrically non-conductive conduit which diverges downstream of an inlet into first and second legs, and re-converges upstream of an outlet, to form a fluid-flow loop between the inlet and the outlet. First and second toroids, each configured as either a drive or a sense coil, are disposed about one of the first and second legs. An electrically non-conductive elongated holder extends into the conduit, to support a temperature detector therein, so that process fluid flowing in the downstream direction passes on opposite sides of, while remaining free of physical contact with, the temperature detector.

A method for measuring the temperature of a process fluid in an electrodeless conductivity sensor, includes providing a non-metallic conduit for the flow of a process fluid in a downstream direction from an inlet to an outlet. The conduit is diverged downstream of the inlet into first and second legs, and re-converged upstream of the outlet to form a fluid-flow loop between the inlet and the outlet. At least one first type toroid is disposed about one of the first and second legs, and at least one second type toroid is disposed about one of the first and second legs, the first type and second type coils being selected from the group consisting of drive and sense coils. An electrically non-conductive holder is extended into the conduit, which supports a temperature detector therein so that process fluid flowing in the downstream direction passes on opposite sides of, while remaining free of physical contact with, the temperature detector.

BRIEF DESCRIPTION OF THE DRAWINGS

The above and other features and advantages of this invention will be more readily apparent from a reading of the following detailed description of various aspects of the invention taken in conjunction with the accompanying drawings, in which.

DETAILED DESCRIPTION

Figure 1:
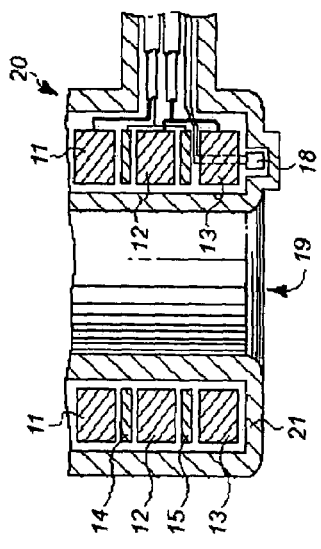
FIG. 1 is a cross sectional elevational view of a portion of an EC sensor of the prior art.

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. The following detailed description is, therefore, not to be taken in a limiting sense, and the scope of the present invention is defined by the appended claims and their equivalents. For clarity of exposition, like features shown in the accompanying drawings are indicated with like reference numerals and similar features as shown in alternate embodiments in the drawings are indicated with similar reference numerals. Where used in this disclosure, the term "axial" when used in connection with an element described herein, shall refer to a direction parallel to the flow path and/or downstream flow of the process solution therethrough. The term "transverse" refers to a direction substantially orthogonal to the axial direction.

In a representative embodiment of the present invention, a fluid to be measured flows through a conduit fabricated from an electrically non-conductive material such as PFA (perfluoroalkoxy polymer resin), PTFE (polytetrafluoroethylene), polyvinyl chloride (PVC), or various combinations thereof, such as perfluoroalkoxy-polytetrafluoroethylene copolymer. Toroidal coils surround the conduit, without physically contacting the fluid. A voltage is supplied to a driver coil, which induces a magnetic field in the fluid flowing within the conduit. This magnetic field similarly induces an electric current in a sensor coil.

A complete loop through which the magnetic field propagates is formed by the fluid itself, via a secondary flow path which diverges from the primary flow path of the conduit upstream from the measuring toroidal coils, and reconverges with the primary flow path of the conduit downstream from the measuring coils. The toroidal coils may be disposed on the primary flow path, the secondary flow path, or both.

The instant inventors have recognized that the sensitivity of the conductivity measurement tends to be adversely affected by the distance the magnetic field must travel through the fluid loop. To compensate for this, embodiments of the invention have been provided with one or more redundant toroidal coils, wired in parallel, to boost induction.

Particular embodiments may also include additional sensor coils disposed upstream and/or downstream of the fluid loop. These additional sensor coils may be wired in reverse phase relative to the driver coils to cancel out stray electrical noise in the system. In addition, a leak detector conductor may optionally be disposed in proximity to the conduit. This conductor may be fabricated from a material sensitive to the process fluid, and may be helically coiled around the conduit, or simply supported parallel thereto. The conductor may then be connected to an Ohmmeter, whereupon any change from a known baseline resistance, such as may occur due to chemical attack by the process fluid, would be indicative of a leak in the conduit.

Figure 2:
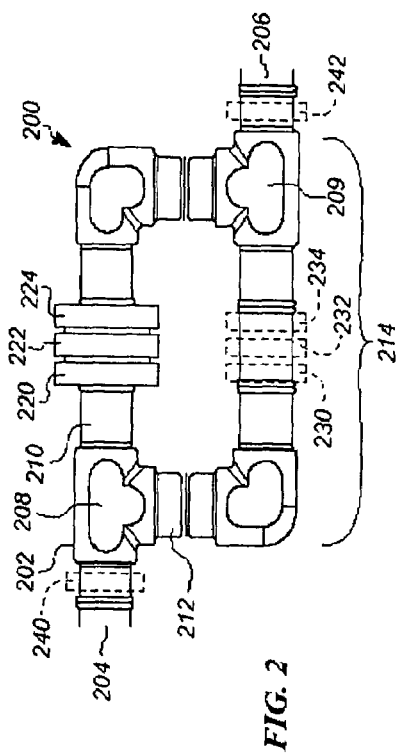
FIG. 2 is an elevational view of an embodiment of the claimed invention, with optional features shown in phantom.

Turning now to the figures, an embodiment of the present invention includes conductivity sensor 200 as shown in FIG. 2. Process fluid flows through conduit 202 in a downstream direction from an inlet 204 to an outlet 206. The conduit diverges at point 208 and forms two flow paths, the primary flow path 210 and the secondary flow path 212. The conduit then reconverges at point 209. The primary flow path 210 and secondary flow path 212 form a fluid-flow loop 214.

In this embodiment, toroids 220, 222, and 224 are located on the primary flow path 210. As described hereinabove, these toroids 220, 222, 224 surround conduit 210 and are physically and electrically isolated from the process fluid flowing through conduit 210. In one embodiment, the central toroid 222 is a sense toroid, and the outer toroids 220, 224 are drive toroids. In another embodiment, the central toroid 222 is a drive toroid, and the outer toroids 220, 224 are sense toroids.

For ease of explanation, the outer toroids 220 and 224 will be designated as drive toroids, and the central toroid 222 will be designated as a sense toroid, with the understanding that the following discussion may also be applicable to the opposite configuration in which the drive and sense toroids are reversed. Electric current supplied to the redundant driver toroids 220, 224 creates a magnetic field which induces an EM field or current which flows through fluid loop (core) 214. This induction similarly induces a current in sense toroid 222, which is proportional to the conductivity of the process fluid.

Use of primary and secondary flow paths 210 and 212 enables the induction loop to be formed by the fluid itself, rather than via a metallic strap as commonly used in the prior art. This enables sensor 200 to measure the conductivity of fluids that tend to attack or are otherwise incompatible with metallic fittings or conductors. Moreover, the use of redundant toroids (either as a drive or sense toroid) as shown, provides enhanced sensitivity which compensates for the adverse affects on sensitivity otherwise associated with relatively high resistance fluid-loop inductive cores.

Optionally, embodiments of the invention may include one or more additional toroids 230, 232, and 234 (shown in phantom) located along fluid loop 214. For convenience, these additional toroids are shown as disposed on secondary flow path 212, but may be substantially anywhere along loop 214. While nominally any combination of drive and sense toroids may be used, in a representative embodiment, toroids 230 and 234 may be operated as drive toroids, with toroid 232 as a sense toroid. These additional toroids may be used in combination, e.g., by wiring them electrically in parallel with respective ones of toroids 220, 222 and/or 224, to further enhance the induction via fluid loop 214.

In another variation of the instant invention, one or more additional sensor toroidal coils 240, 242 may be disposed upstream and/or downstream of fluid loop 214. These sensor coils 240, 242 may be wired in reverse phase with the other (on-loop) sense coils 222, 232, etc., to effectively cancel out electrical noise which may be present in the conduit 210 outside fluid loop 214.

Figure 3:
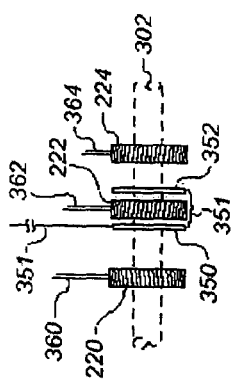
FIG. 3 is an exploded view, with portions shown in phantom, of the embodiment of FIG. 2.

Turning now to FIG. 3, one set of three toroids, e.g., toroids 220, 222 and 224, is shown in an exploded view. As shown, toroids 220 and 224 may be connected in parallel to a source of electric current via cables 360, 364, to function as drive toroids. Toroid 222 is connected by cable 362 to a conventional analysis apparatus, such as the 875EC Series Analyzers or 870ITEC Series Transmitters (Invensys Systems Inc., Foxboro, Mass.) which may be further coupled to a conventional factory automation system.

As also shown, shields 350, 352, may be interspersed between the toroids to help prevent the fields generated by the drive toroids from interfering with one another and/or with the sense toroids. In desired embodiments, these magnetic shields 350, 352 extend circumferentially about conduit 302, while remaining physically and electrically isolated from the process fluid flowing therethrough. For example, in particular embodiments magnetic shields 350, 352 are centrally apertured discs, in the form of copper washers. Ground wire 351 connects shields 350, 352 to one another, and to ground.

Figure 4:
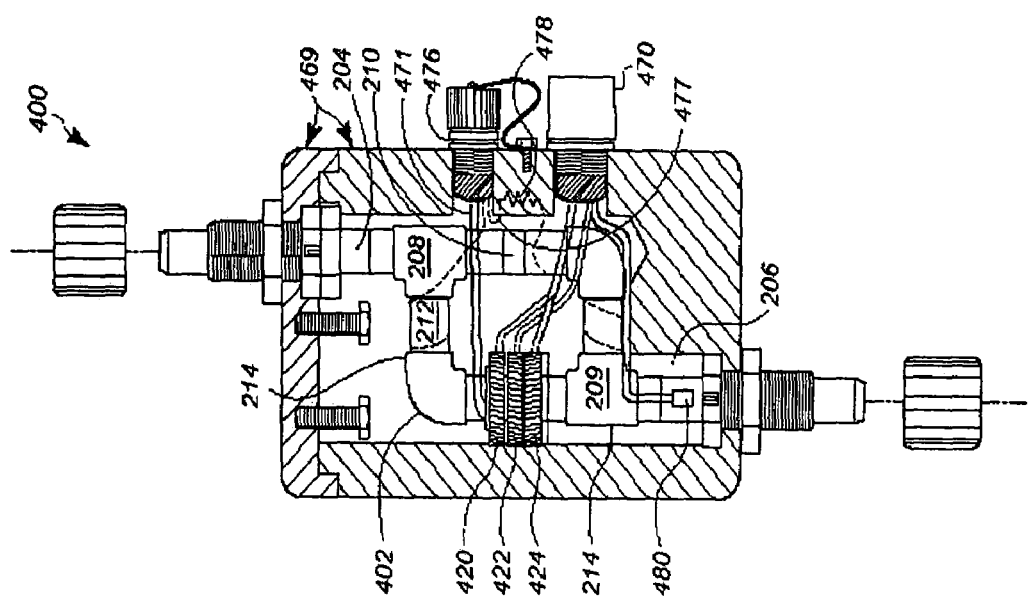
FIG. 4 is a partially cross-sectional elevational view of an alternate embodiment of the claimed invention, with optional portions thereof shown in phantom.
Figure 5:
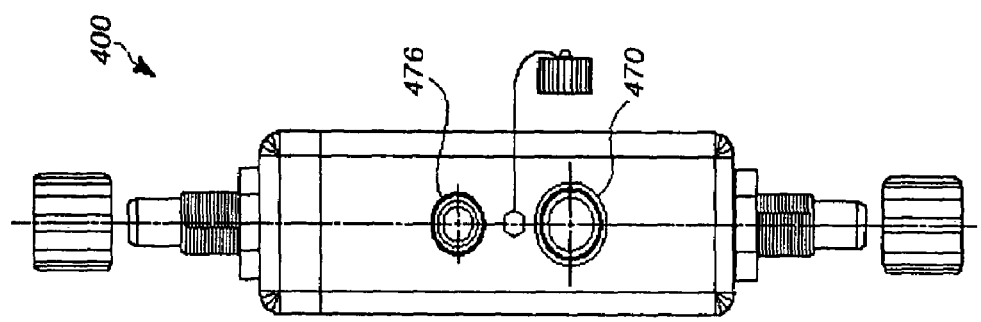
FIG. 5 is a plan view of the embodiment of FIG. 4.

Referring now to FIGS. 4 & 5, any of the aforementioned embodiments may be disposed within a housing 469, to form an enclosed conductivity measurement device shown at 400. In this embodiment, driver toroids 420, 424 and sense toroid 422 are coupled to a modular connector portion 470 to facilitate removable connection to a transmitter or other data capture/calculation device or system. Connector portion 470 may be nominally any connector type known to those skilled in the art. A test port 476 is also shown, which may be coupled to opposite ends of a calibration conductor 471 of known resistance, which forms a loop passing through the toroids as shown. Calibration conductor 471 may be used to calibrate device 400 by shorting the ends thereof (e.g., using a calibrator plugged into test port 476), and then operating the device without process fluid in fluid loop 214. The output of the sensor toroids may then be calibrated to match the known resistance of conductor 471, as will be discussed in greater detail hereinbelow. Those skilled in the art should recognize that this calibration port/conductor, and any other aspects shown and described with respect to a particular embodiment, may be applied to any other of the embodiments described herein, without departing from the spirit and scope of the present invention.

As also shown, an optional leak detection conductor 477 (shown in phantom) may be provided. The conductor 477 may be disposed at substantially any location likely to come into contact with process fluid leaking from conduit 402. In the embodiment shown, conductor 477 may be disposed at any convenient location within housing 469, such as at the lowest installed location thereof, i.e., at the point at which any leaked process fluid would collect. In addition, or alternatively, conductor 477 may be extended alongside, or wrapped helically around conduit 402 as shown in phantom. This latter approach may be particularly useful in embodiments not having a housing 469.

Conductor 477 may be fabricated from a material sensitive to the particular process fluid under test. For example, since many of the embodiments described herein are intended to measure the conductivity of process fluids such as caustic acids (e.g., HF, HCl) that chemically attack various types of metals (e.g., aluminum), conductor 477 may be fabricated from such a metal. The resistance of conductor 477 may then be monitored, e.g., via terminals C & D (FIG. 6) of test port 476, to measure any changes in resistance which may be indicative of fluid having leaked from conduit 402 and contacted conductor 477. For example, an increase in measured resistance may occur due to chemical attack and an associated reduction in cross-sectional area of the conductor 477.

As a further option, conductor 477 may also include a discrete resistor 478 (shown in phantom) as desired to customize the baseline resistance. A resistor 478 may be chosen to increase the baseline resistance beyond the expected resistance of the process fluid. Contact with any leaked process fluid of lower resistance would tend to decrease the measured resistance at test port 476, to indicate the presence of the leak. This configuration may be particularly useful when measuring a process fluid that does not chemically attack conductor 477, but is nevertheless incompatible with metals, such as due to contamination/purity concerns.

Although leak detection conductor 477 and optional resistor 478 are shown and described as incorporated within the various conductivity sensors of the present invention, those skilled in the art should recognize that it may be used independently and/or in combination with nominally any type of fluid sensor, without departing from the spirit and scope of the present invention. For example, leak detection conductor 477 and/or resistor 478 may be incorporated with various temperature detectors, pressure detectors, conductivity sensors, pH sensors, ORP sensors, flow meters, and combinations thereof. Commercial examples of such devices include the 83 Series Vortex Flowmeters, I/A Series Pressure Transmitters, 134 Series Intelligent Displacement Transmitters, I/A Series Temperature Transmitters, 873 Series Electrochemical Analyzers, and the 871 Series conductivity, pH and ORP sensors all commercially available from Invensys Systems, Inc. of Foxboro, Mass.

As also shown, a temperature sensor 480, such as a conventional resistance temperature detector (RTD), may be physically coupled to the conduit to detect the temperature of the process fluid, and electrically coupled to connector 470.

Figure 6:
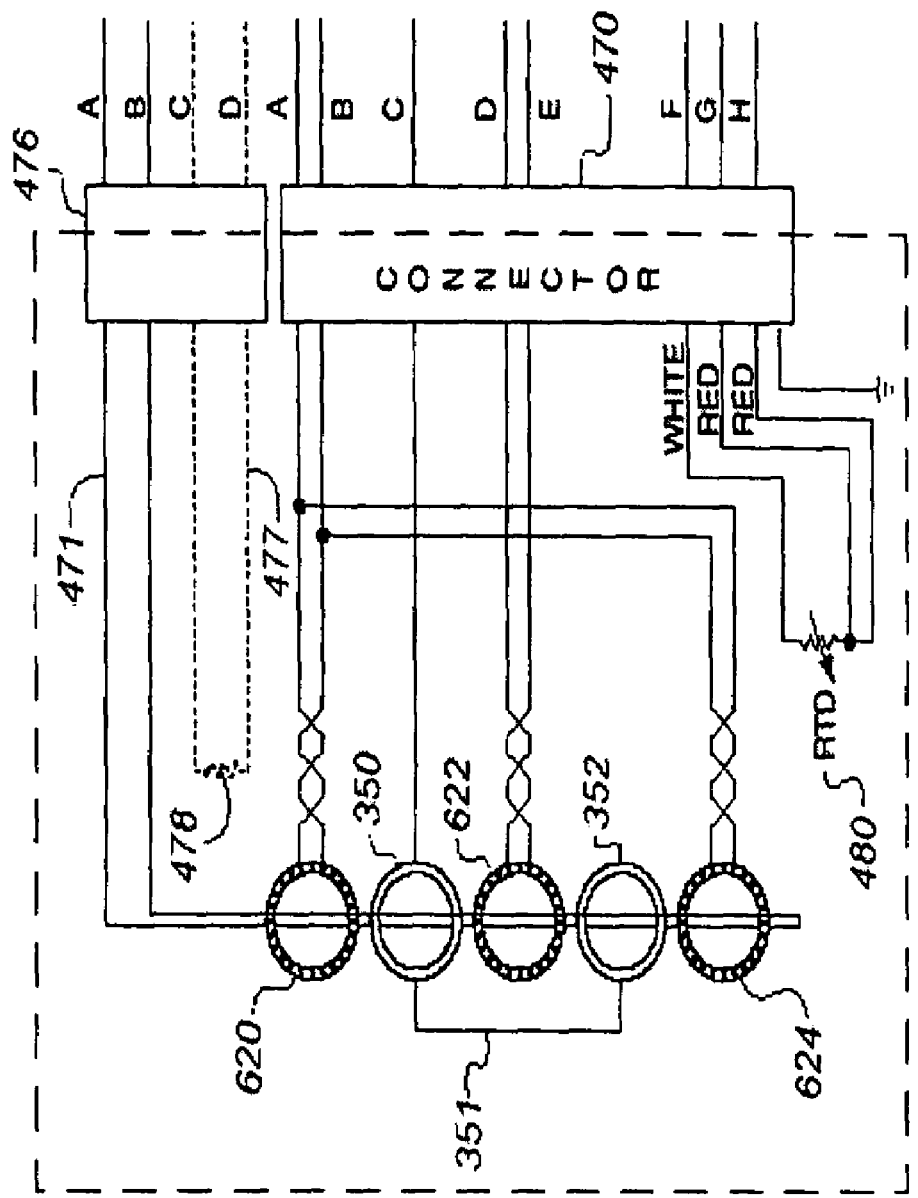
FIG. 6 is an exemplary wiring schematic of an embodiment of the present invention.

Turning now to FIG. 6, sensor 200 (FIG. 2) or 400 (FIG. 4) may be wired by connecting drive toroids (shown at 620, 624) to legs A and B of connector 470. Sense toroid (shown at 622) may be connected to legs D and E of the connector 470. The optional magnetic shields 350, 352 may be connected to leg C of the connector. Temperature sensor or thermosensor 480 may be connected to legs F, G, and H of connector 470.

Calibration conductor 471 extends from terminal A of the test port 476 through toroids 620, 622, 624, and returns to terminal B thereof. Optional leak detection conductor 477 (shown in phantom), with or without resistor 478, extends from leg C of port 476, into leak-contacting proximity to the conduit, and in spaced relation from the toroids, and returns to leg D of the calibrator.

Figure 7:
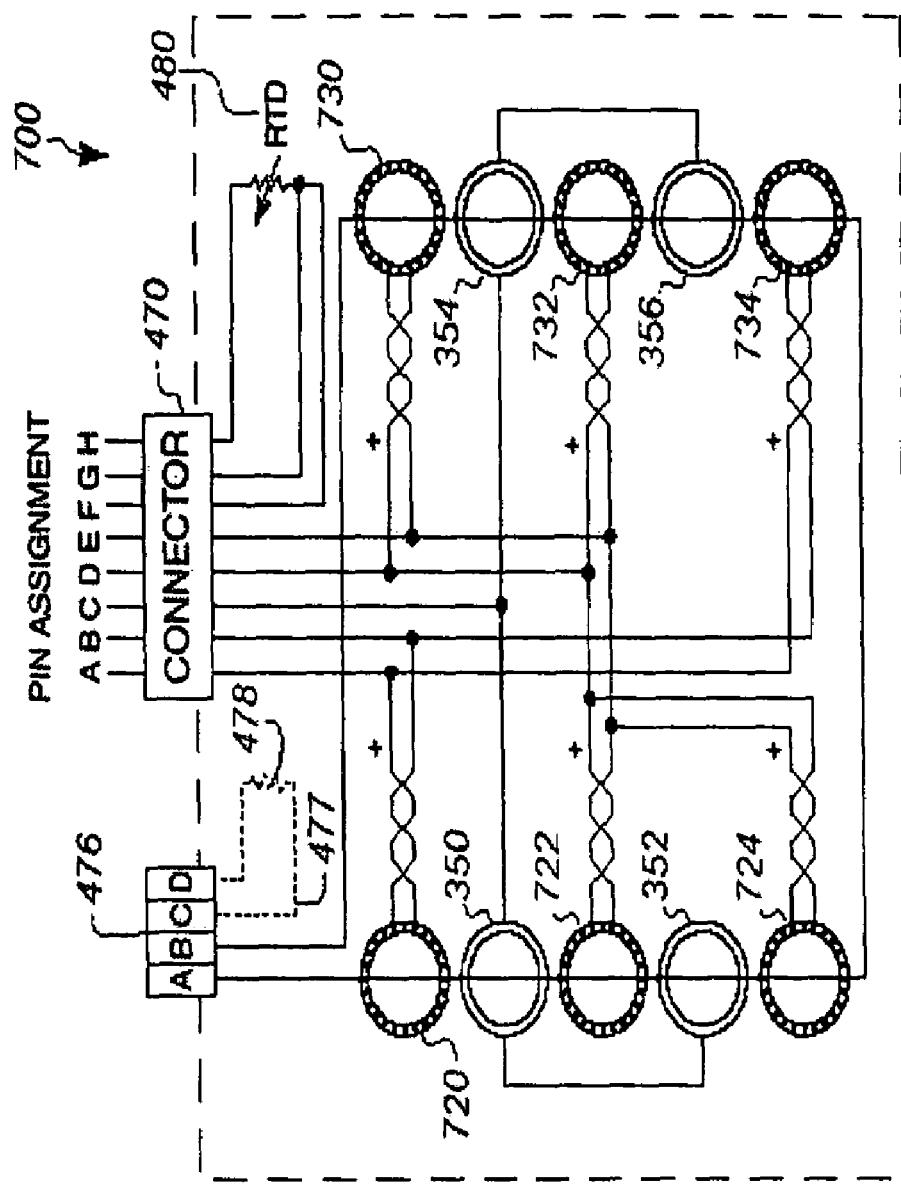
FIG. 7 is an exemplary wiring schematic of an alternate embodiment of the present invention.
Figure 8:
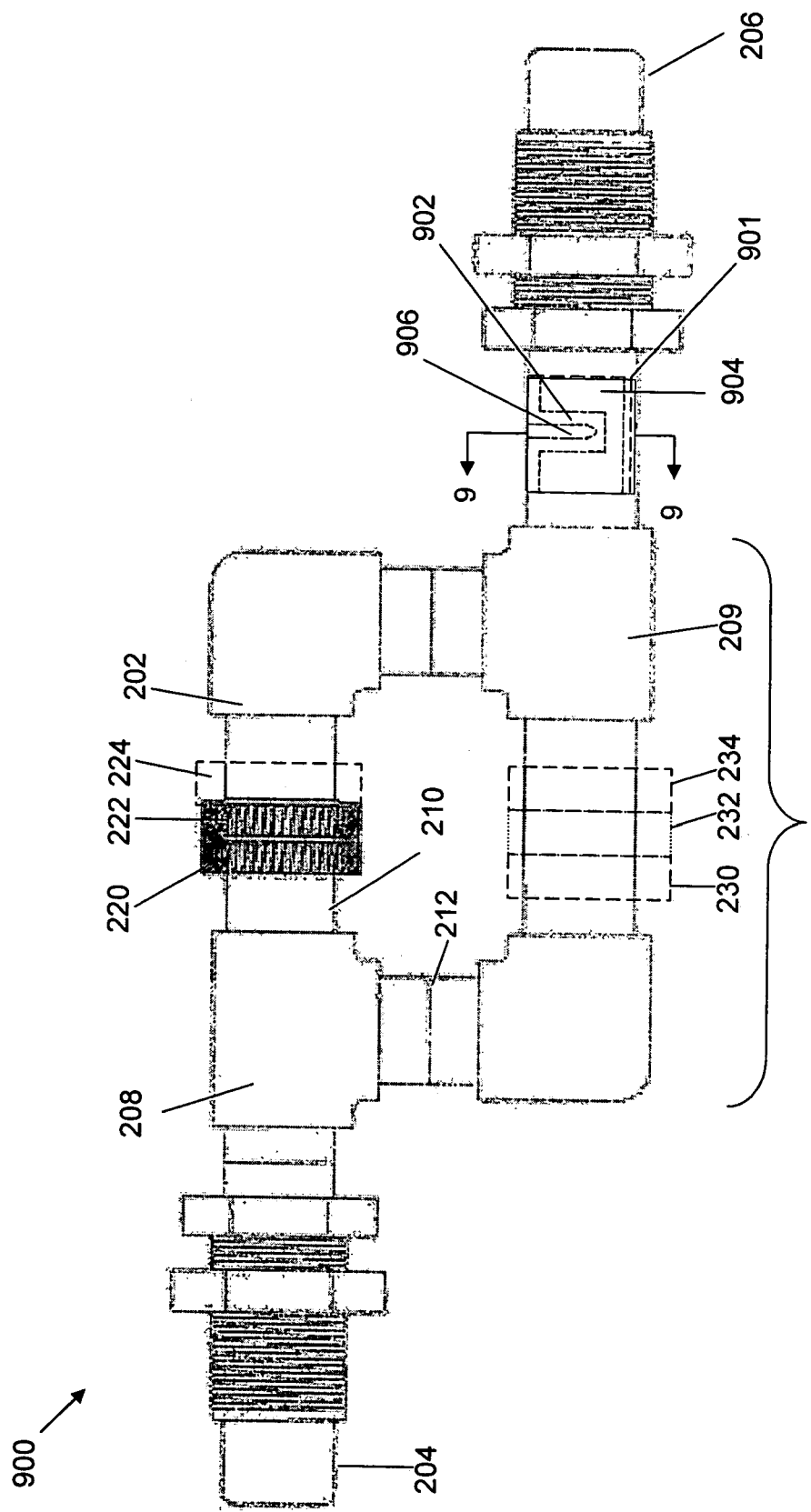
FIG. 8 is a partially broken away elevational view, with optional portions shown in phantom, of an alternate embodiment of the present invention.

FIG. 7 shows a wiring schematic of an embodiment substantially similar to those shown and described hereinabove with respect to FIGS. 2 & 4, in which the principal flow path 210, and optionally, the secondary flow path 212, each include one drive toroid and two sense toroids. As shown, drive toroids 720, 734 are connected to terminals A and B of connector 470. Sense toroids 722, 724, 730, 732 are connected to legs D, E of connector 470. Copper washers 350, 352, 354, 356 serve as magnetic shields between the toroids and are grounded at terminal C of connector 470. RTD 480 serves as a thermosensing means and is connected to terminals F, G, H of connector 470. Optional leak detection conductor 477 (shown in phantom), which may include resistor 478, may be connected to terminals C and D of test port 476 as shown.

Embodiments of the invention having been described, the operation thereof will be discussed with reference to the following Table I.

TABLE I

| | |
|---|---|
| 802 | fasten conduit ends 204 and 206 in process flow line |
| 804 | couple connector 470 to a data capture device/processor |
| 806 | calibrate by shorting terminals A & B of test port |
| 810 | activate drive coils |
| 812 | capture current of sense coils |
| 814 | calculate measured conductivity value |
| 815 | map calculated conductivity value to known conductivity of the calibration loop |
| 816 | disable calibration loop |
| 818 | initiate process flow |

TABLE I-continued

| | |
|---|---|
| 819 | repeat steps 810, 812 and 814, to generate conductivity values for the process fluid. |
| 820 | Optionally monitor system for leakage |

As shown, conduit ends 204 and 206 are fastened 802 in series with a process flow line, and connector 470 is coupled 804 to a data capture device/processor such as an analyzer of the type available commercially from Invensys Systems, Inc., as discussed hereinabove. The sensor may then be calibrated 806, e.g., using a conventional calibrator coupled to test port 476, which shorts terminals A & B thereof to provide a closed induction loop of known resistance as described hereinabove. Thereafter, a current may be fed 810 to terminals A & B of connector 470, to activate the drive coil(s) in parallel with one another, to induce an EM field in the calibration loop, and in turn, induce a current in the sense coils. Since the sense coil(s) are similarly wired in parallel with one another, a single current value may be captured 812 at terminals D & E of connector 470. This captured current value may then be used in a conventional manner to calculate 814 a measured conductivity value. The calculated conductivity value is then adjusted or mapped 815 to the known conductivity of the calibration loop. Once calibrated, terminals A & B of test port 476 are disconnected 816 from one another to disable the calibration loop, and process fluid is permitted to flow 818 through the device. Steps 810, 812 and 814 are then repeated 819, to generate conductivity values for the process fluid. Optionally, the flow conduit may be monitored 820 for leakage, by periodically checking for any deviation from baseline resistance of leak detection conductor 477 and/or resistor 478. As described hereinabove, the use of parallel fluid flow paths provides a completely fluidic induction loop that eliminates the need for any metallic conductors to contact the process fluid. This, in turn, enables the conductivity measurement of process fluids that are incompatible with metals. In addition, the redundancy of drive and/or sense coils serves to enhance induction within the fluidic loop for improved measurement sensitivity and/or accuracy.

Moreover, although use of connector 470 is shown and described herein, one should realize in light of the instant disclosure, that embodiments may be hard-wired, e.g., to obviate any need for connector 470, without departing from the spirit and scope of the present invention.

Another optional aspect of the invention includes a temperature detection means that may be used in combination with any of the electrodeless conductivity sensors described herein (including, for example, sensors 200, 400) and including embodiments having as few as a two toroids. As discussed hereinbelow, in particular embodiments, this temperature detection means includes an electrically non-conductive holder configured for extending into fluid flow conduit 202. The holder supports a temperature detector therein so that process fluid may flow on opposite sides of the detector while the detector itself remains free of physical contact with the fluid. This aspect enables these embodiments to be used in applications in which the process fluid is incompatible with the metallic materials from which the temperature detector may be fabricated.

As mentioned above, the inventors found that disposing a temperature detector on, or embedded within, the wall of a polymer conduit resulted in temperature measurements that were too slow and/or inaccurate for many applications. This may be true even in the event a polymer-encapsulated RTD was placed on the interior surface of the conduit.

The instant inventors discovered that despite the relatively high thermally insulative value of many conventional polymers, surprisingly fast and accurate temperature response could be obtained by placing an RTD within a relatively thick-walled polymeric holder, and placing the holder within the conduit in a manner that enabled process fluid to pass on either side thereof. These levels of desired accuracy and response time were provided even when the walls of the holder were as nominally as thick as the walls of the polymeric conduit.

The effectiveness of this approach was also surprising, given the relatively large percentage of cross-sectional area of the flow path that was blocked by the relatively large thickness of the polymeric holder. Indeed, it was found that desirably fast and accurate results were provided, without clogging the flow path, even when the holder effectively blocked up to about 50% to 60% of the cross-sectional area of the flow path.

Turning now to FIGS. 8-11, an example of the inventive temperature detection means is shown and described in connection with an electrodeless conductivity sensor 900. Sensor 900 is similar to sensors 200, 400, discussed above, though including as few as two toroids 220, 222 configured as drive and sense coils. Sensor 900 may optionally include any number of additional toroids 224, 230, 232, 234, as shown in phantom and as described hereinabove. Toroids 240, 242 (FIG. 2) may also be disposed outside of the fluid loop 214 as discussed above.

As shown, exemplary temperature detection means includes a detector 906 supported within a holder 902 which extends into the process flow, e.g., in a direction substantially transverse to the downstream direction of the flow. Holder 902 is sealed in a fluid-tight manner to conduit 202, and otherwise surrounds and thus physically isolates or encapsulates detector 906 from the process fluid, to protect against chemical attack and metallic contamination of process fluid.

The holder may be fabricated from any suitable material. For example, polymers such as PFA (perfluoroalkoxy polymer resin), PTFE (polytetrafluoroethylene), polyvinyl chloride (PVC), or combinations thereof such as perfluoroalkoxy-polytetrafluoroethylene co-polymer, may be suitable for use with many process fluids that are generally incompatible with metals such as hydrofluoric acid, hydrochloric acid, hydrogen peroxide, nitric acid, sulphuric acid, TMAH (tetramethylammonium hydroxide), ammonium hydroxide, etc. Also, any number of conventional temperature detectors may be used, such as the Model No. 29348-T01-12, or Model No. 29348-T10-12 RTDs available from RdF Corporation, Hudson, N.H.

Holder 902 may be optionally removable from the conduit 202, e.g., to facilitate placement at a variety of locations within conduit 202, such for monitoring temperatures remotely from loop 214, or to provide redundant temperature monitoring. Convenient removal may also be desired to facilitate periodic maintenance including cleaning or replacement. In this regard, holder 902 may be disposed within a modular adapter 901 in the form of a conduit section sized and shaped to mate in-line at nominally any location within conduit 202. Adapter 901 may thus be inserted between the junction of any two sections of conduit 202, simply by using conventional pipe flanges or threads (not shown) or other pipe joining techniques including bonding with adhesives. In this manner, holders and RTDs may be conveniently placed at nominally any number of desired locations within or without fluid loop 214. In addition, a plurality of adapters 901 with holder/detector combinations may be used at various locations along conduit 202 to provide redundant temperature monitoring. In particular embodiments, holder 902 may be fabricated integrally with adapter 901, e.g., by gluing, welding or otherwise bonding to one another, or by fabricating as a one piece molded device, to help prevent process fluid from leaking between the holder and adapter.

Figure 9:
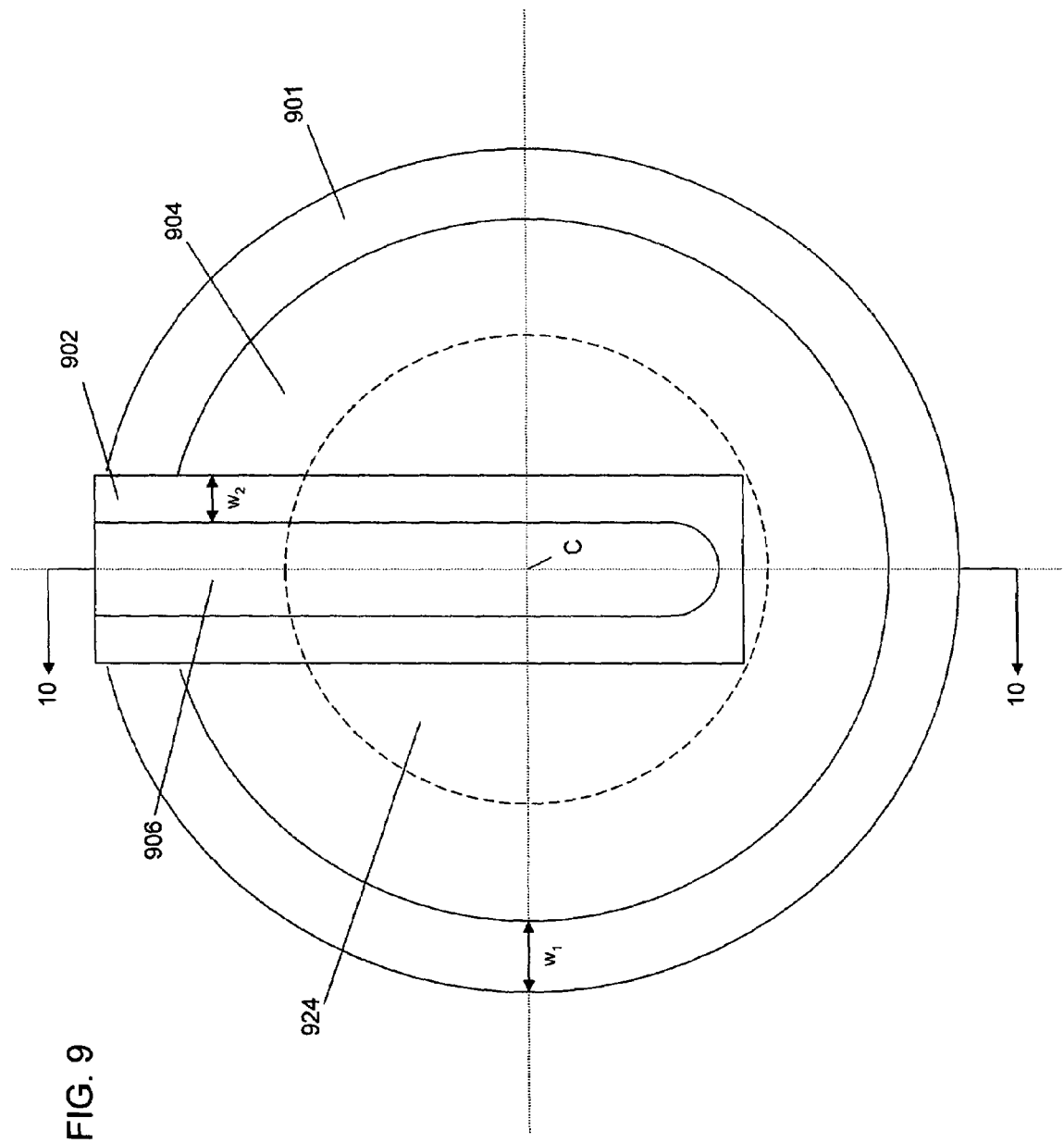
FIG. 9 is a cross sectional view, on an enlarged scale, taken along 9-9 of FIG. 8.
Figure 10:
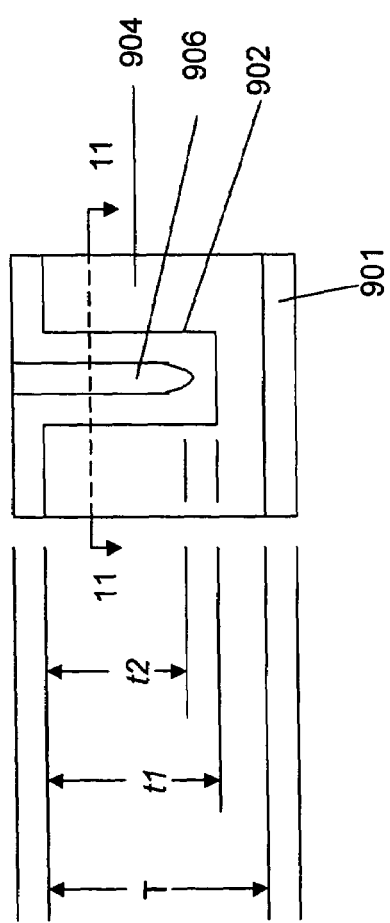
FIG. 10 is a cross sectional view, on a reduced scale, of a portion of the alternate embodiment taken along 10-10 of FIG. 9.
Figure 11:
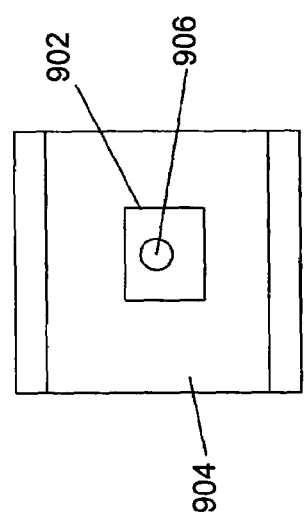
FIG. 11 is a cross sectional view taken along 11-11 of FIG. 10.

As best shown in FIG. 9, holder 902 may be configured to place detector 906 nominally anywhere within at least the middle 50 percent (shown at 924) of the transverse cross sectional area of passage 904. In particular embodiments, however, it may be desired to extend detector 906 into the middle 25 percent of cross-sectional area, while in particularly desired embodiments, it may be advantageous to ensure that detector 906 intersects the center C of the cross-sectional area of passage 904 as shown.

Extending temperature detector 906 into at least middle area 924 has been found to be desirable in many applications because the flow rate of the process fluid tends to be highest near the center of the flow path, and this higher flow rate tends to enhance heat transfer from the process fluid to the temperature detector 906. Such a central location also tends to minimize any effects of ambient external temperatures acting on the conduit wall.

The wall thickness $w_2$ of holder 902 should be large enough to ensure adequate structural resistance to the pressure of the particular process fluid. This wall thickness should also be large enough to adequately limit permeability of the process fluid into holder 902. The permeability of the holder 902 wall generally decreases as a function of the increase of the square of wall thickness $w_2$.

In light of the instant disclosure, it should be evident that the determination of particular wall thickness $w_2$ may depend on the particular application, e.g., on the particular process fluid, fluid velocity, fluid pressure, and the material from which the holder is fabricated. However, it has been found that wall thicknesses $w_2$ of the holder may be as large as the typical wall thickness (fabricated from the same material) of conventional conduits 202, (e.g., as in Example 3 below), while still maintaining desired levels of temperature measurement accuracy and response time. Wall thickness $w_1$ of adapter 901 may be of similar dimension. Use of such common materials and wall thicknesses tends to simplify construction, e.g., by nominally ensuring that the holder has sufficient structural integrity and impermeability to ensure reliable operation in many applications. The successful use of such relatively large wall thicknesses $w_2$ is somewhat counterintuitive because the thermal conductivity decreases as the wall thickness increases, and because the thicker walls block a relatively higher percentage of the transverse cross sectional area of the passage 904, which one may also expect to adversely affect response time.

Figure 12:
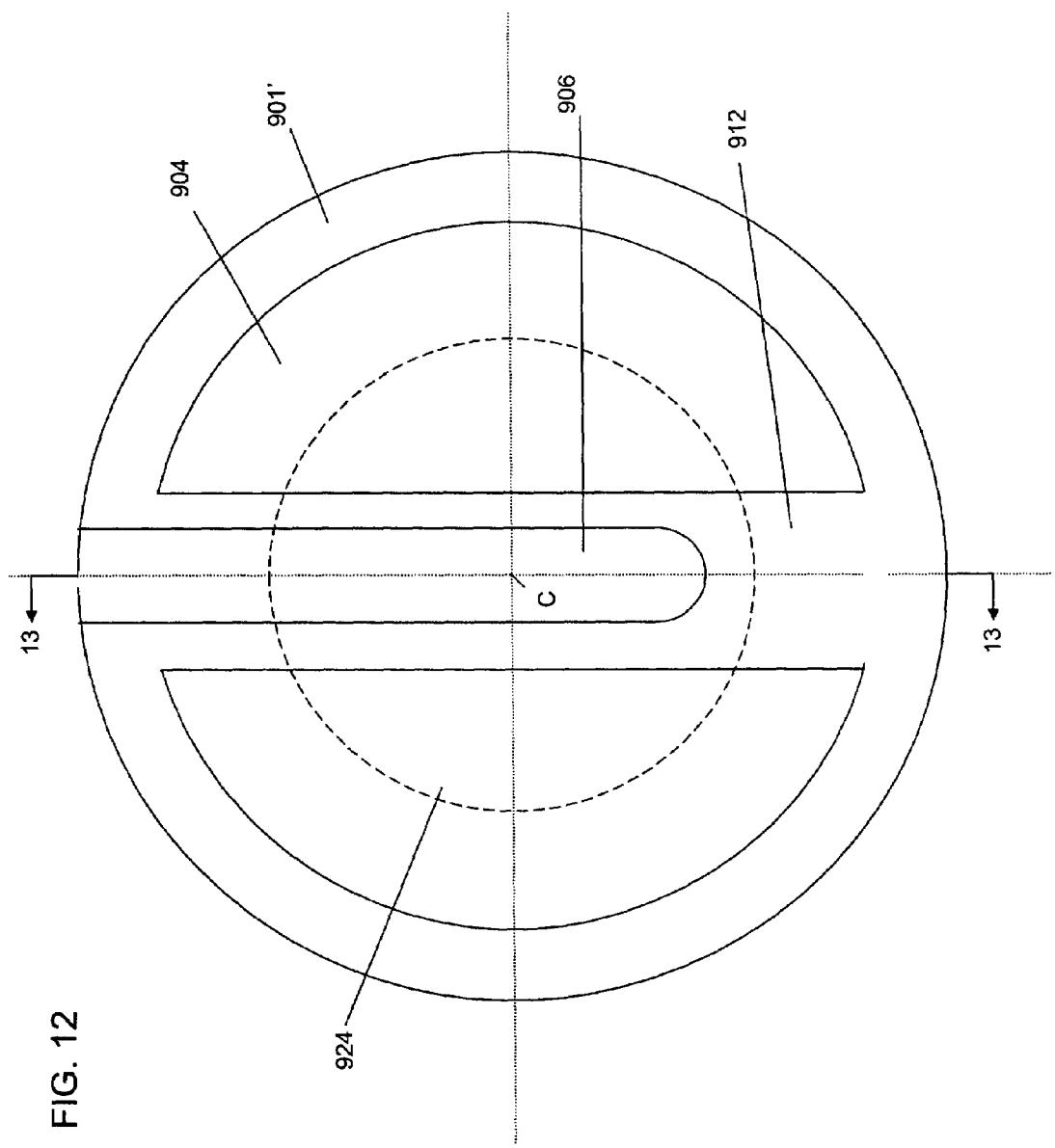
FIG. 12 is a cross sectional view of an alternate embodiment of the present invention, taken along 9-9 of FIG. 8.
Figure 13:
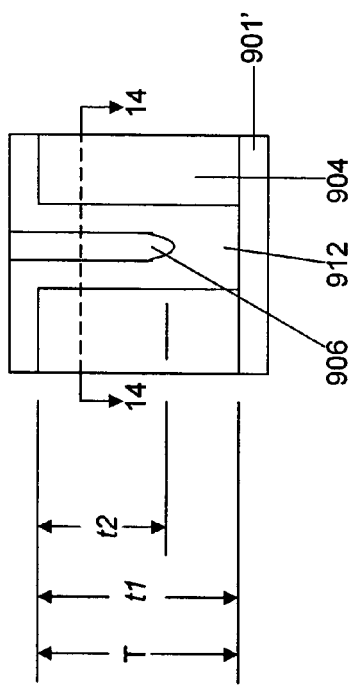
FIG. 13 is a cross sectional view, on a reduced scale, of a portion of the embodiment of FIG. 12, taken along 13-13 of FIG. 12.
Figure 14:
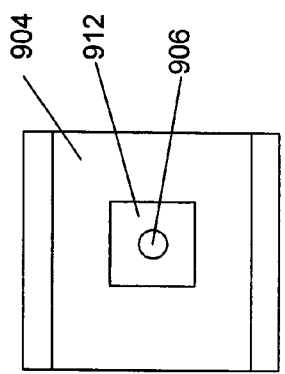
FIG. 14 is a cross sectional view of the embodiment of FIG. 12, taken along 14-14 of FIG. 13.

Turning now to FIG. 12, an alternate embodiment of a holder, shown at 912, is substantially similar to holder 902, but extends entirely across passage 904, e.g., across the entire inner diameter of an adapter 901' which is otherwise substantially similar to adapter 901. This embodiment may be desired for use in relatively smaller diameter conduits, as it tends to maximize the cross-sectional area of the passage 904 into which the temperature detector 906 may extend, for enhanced contact area with the process fluid. As with holder 902, this holder 912 enables temperature detector 906 to extend to nominally anywhere within at least the middle 50 percent 924 of the transverse cross sectional area of passage 904. In various embodiments, however, it may be desired to extend detector 906 into the middle 25 percent of cross-sectional area, while in particularly desired embodiments, it may be advantageous to extend detector 906 through the center C of the cross-sectional area of passage 904 as shown.

Figure 15:
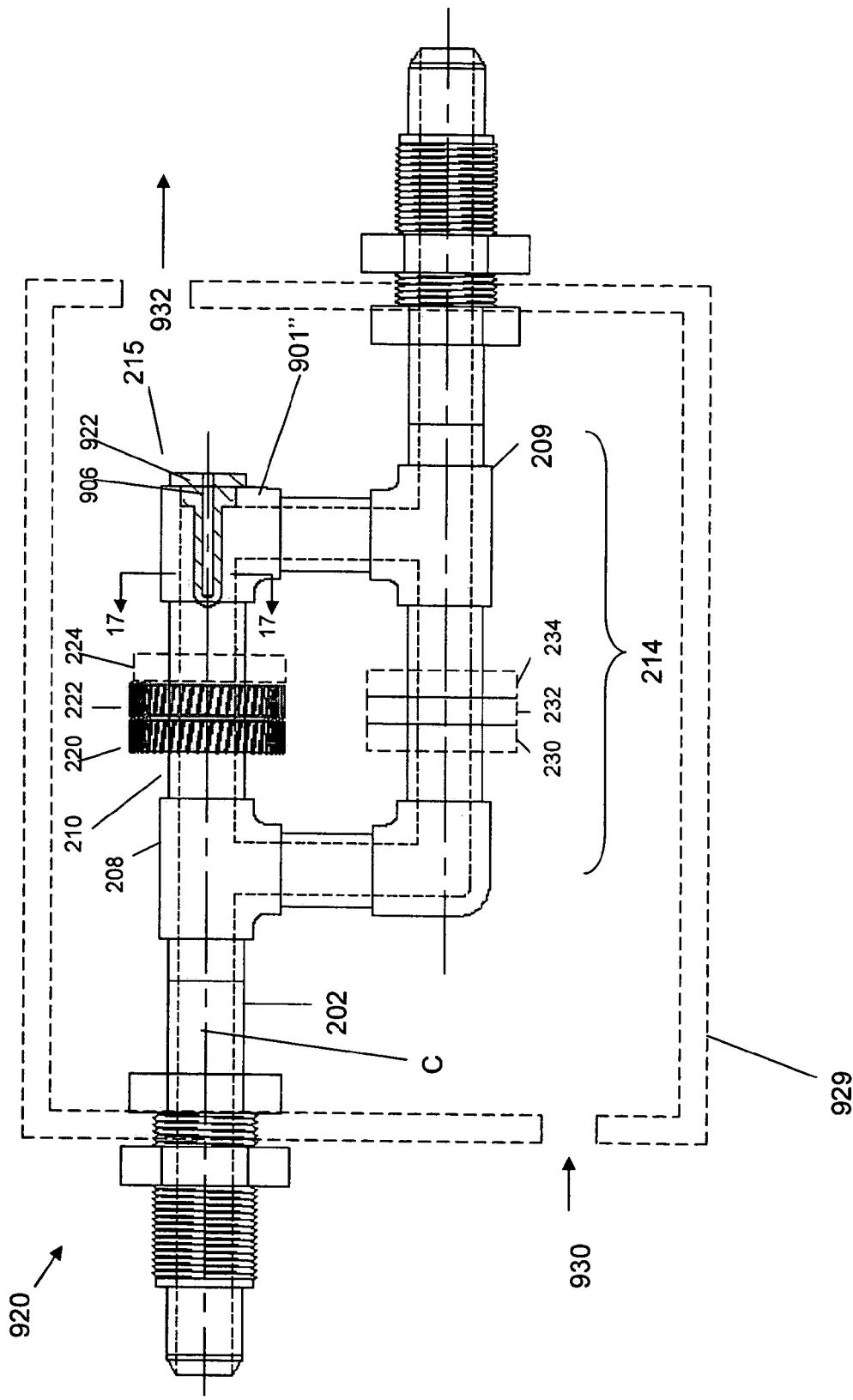
FIG. 15 is a partially broken away elevational view, with optional portions shown in phantom, of yet another embodiment of the claimed invention.
Figure 16:
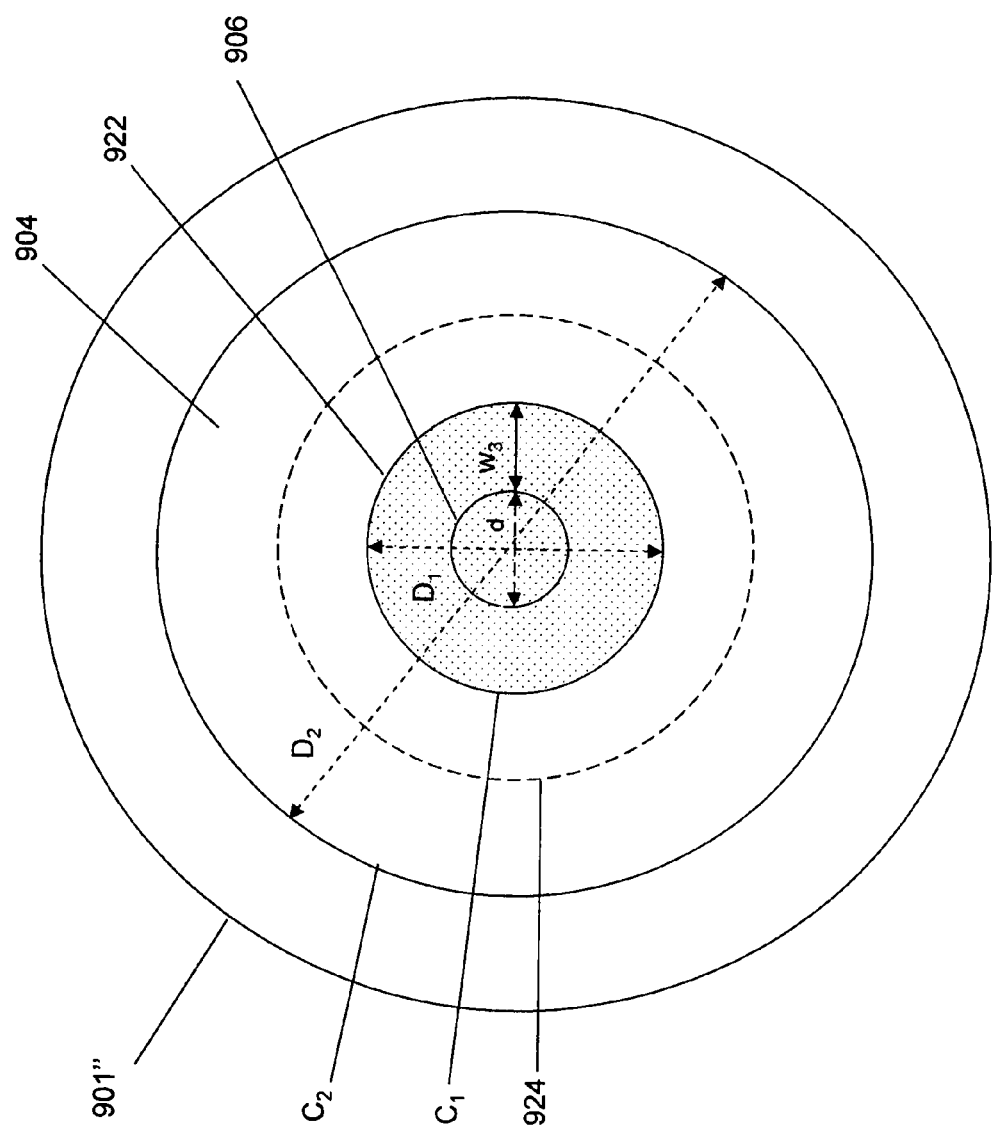
FIG. 16 is a cross sectional view, on an enlarged scale, taken along 16-16 of FIG. 15.
Figure 17:
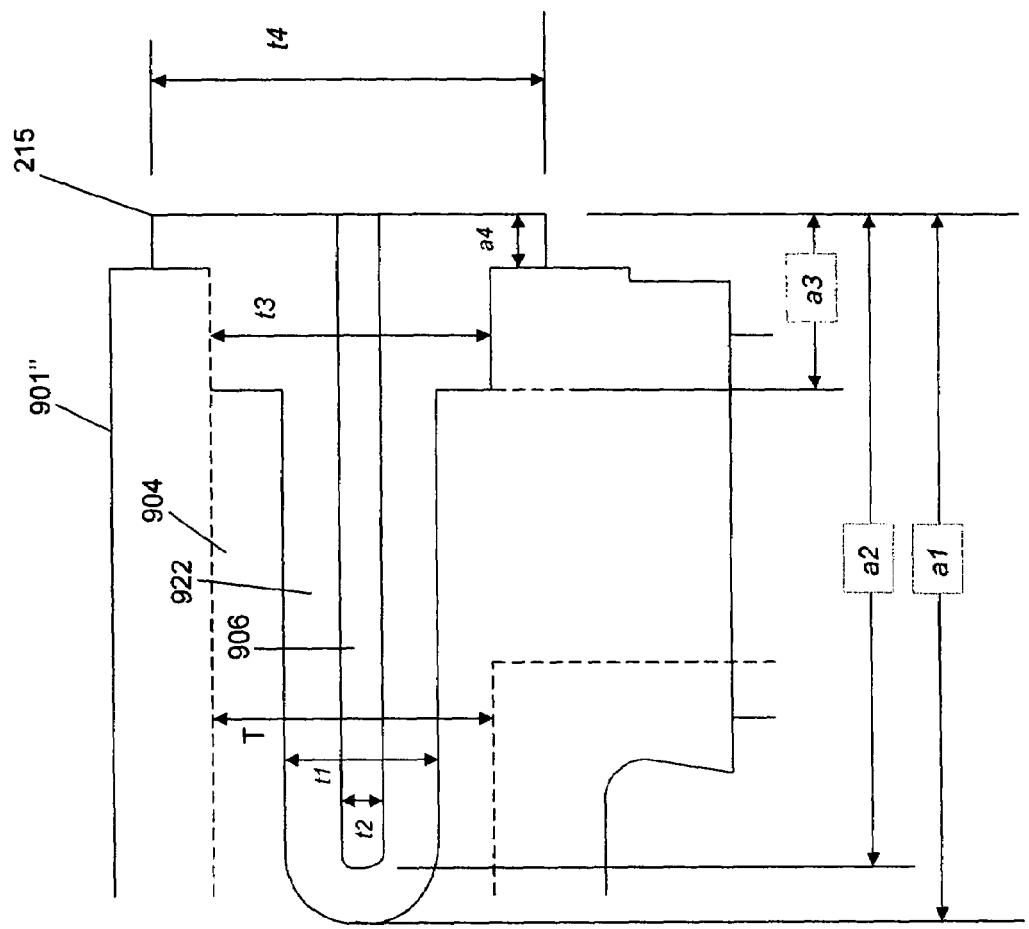
FIG. 17 is an elevational view, on an enlarged scale, of a portion of the embodiment of FIG. 15.

Referring now to FIGS. 15-17, the temperature detector may alternatively extend into the passage in direction which are not transverse to the downstream direction. For example, holder 922 extends nominally parallel to a portion of conduit 202 as shown. In such an embodiment, sensor 920 includes a holder 922 disposed in an adapter 901". Adapter 901" is disposed in the form of a conduit elbow or "T" 215 configured for placement in a corner of fluid loop 214. In this manner, holder 922 extends into, and parallel with a portion of flow loop 214, e.g., substantially parallel with the downstream direction as shown by centerline C. As with holders 902, 912 discussed hereinabove, holder 922 also supports temperature detector 906 so that process fluid may flow along opposite sides thereof. In addition, this holder 922 also permits the use of relatively longer detectors and/or smaller diameter flow conduits. For example, this configuration may particularly be desirable for use in applications involving conduits having a cross-sectional dimension smaller than the effective length of the temperature detector 906, as shown.

As best shown in FIG. 16, temperature detector 906 may be disposed generally within the center of flow path 904, e.g., at least within the middle 50 percent of the transverse cross sectional area of the passage 904, such as shown by dashed circle 924. As discussed herein with reference to FIG. 9, disposing the temperature detector 906 within this middle area 924 tends to enhance temperature measurement speed and accuracy due to the generally higher flow rate near the center of the flow path and associated higher thermal transfer effects, and because the effects of ambient external temperature being conducted through the conduit wall are minimized. In particular embodiments, it may be desired to enhance these aspects by ensuring placement of detector 906 within the middle 25 percent of cross-sectional area, and/or by extending detector 906 through the geometric center C of the cross-sectional area of passage 904 as shown.

As discussed above with respect to wall thicknesses $w_2$, the wall thickness $W_3$ of holder 922 is large enough to provide holder 922 with sufficient structural integrity to resist the pressure and permeability of the particular process fluid being measured. Moreover, this thickness may be chosen, in combination with the size (e.g., diameter d) of RTD 906, to provide a transverse cross-section having an area of up to about 50 to 60 percent that of passage 904 (shown at $C_2$). For example, in the event a holder 922 of circular cross-section is used, as shown, the holder's cross-sectional area $C_1$ is a function of transverse dimension $D_1$, which in turn, is a function of wall thickness $W_3$ and transverse dimension d of temperature detector 906 including any clearance therebetween. As with the embodiments discussed hereinabove, it has been found that holder 922 may be fabricated from the same material, with walls $W_3$ of the same thickness as those of conventional polymer conduits 202, while still maintaining desired levels of temperature measurement accuracy and response time. The wall thicknesses of adapters 901, 901', and 901" may also be similar to those of conduit 202 and/or holders 902, 912, 922.

Table 2 shows the percent blockage created with holders of varying wall thicknesses $w_3$ and temperature detectors of diameter d of 0.070 inches, disposed within a passage having an inner diameter $D_2$ of 0.354 inches.

TABLE 2

| $w_3$ (inches) | d (inches) | $C_1$ (inches$^2$) | $D_2$ (inches) | $C_2$ (inches$^2$) | Blockage (%) |
|---|---|---|---|---|---|
| 0.065 | 0.070 | 0.0314 | 0.354 | 0.0984 | 31.91 |
| 0.075 | 0.070 | 0.0380 | 0.354 | 0.0984 | 38.62 |
| 0.085 | 0.070 | 0.0452 | 0.354 | 0.0984 | 45.93 |

Table 2 shows that for a holder in which d=0.070 in., and $C_2$=0.0984 in$^2$, a $w_3$ dimension of 0.085 in. has a cross-sectional area of less than 50 percent that of the fluid flow passage.

Turning back to FIG. 15, in any of the embodiments disclosed herein, it may be desirable to place sensitive components, such as toroids 220, 222, etc., within an optional protective enclosure such as shown in phantom at 929. However, as discussed, many of these embodiments may be used with process fluids capable of permeating or diffusing, over time, into the polymeric structure of the various materials used for conduits 202, etc. By the time they reach the outer surface of the conduit, the diffused materials are generally in sufficiently low concentrations to dissipate harmlessly along lengths of conduit. However, the gases may undesirably tend to accumulate in confined spaces. Accordingly, enclosure 929 may be provided with vents or ports, such as shown at 930, 932, which may be used to provide natural or forced (e.g., fan fed) ventilation. It should be noted that depending on the fluid, the enclosure 929 may be either vented to atmosphere, e.g., in the event the diffused gas is a non-pollutant, or alternatively, may be captured by a conventional gas recapture and/or filtration system.

Figure 18A:
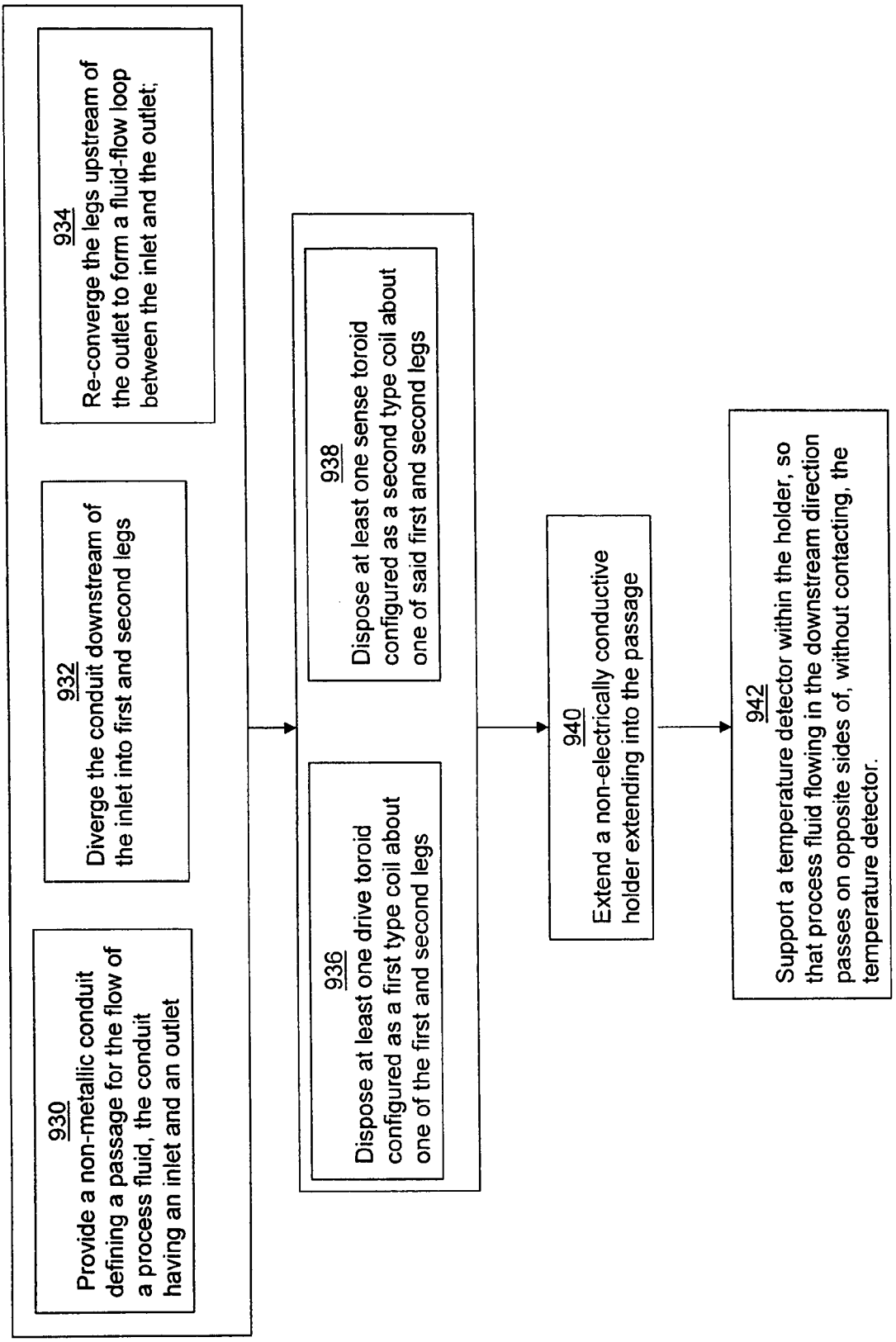
FIGS. 18A and 18B are flow charts of an exemplary method of the present invention.
Figure 18B:
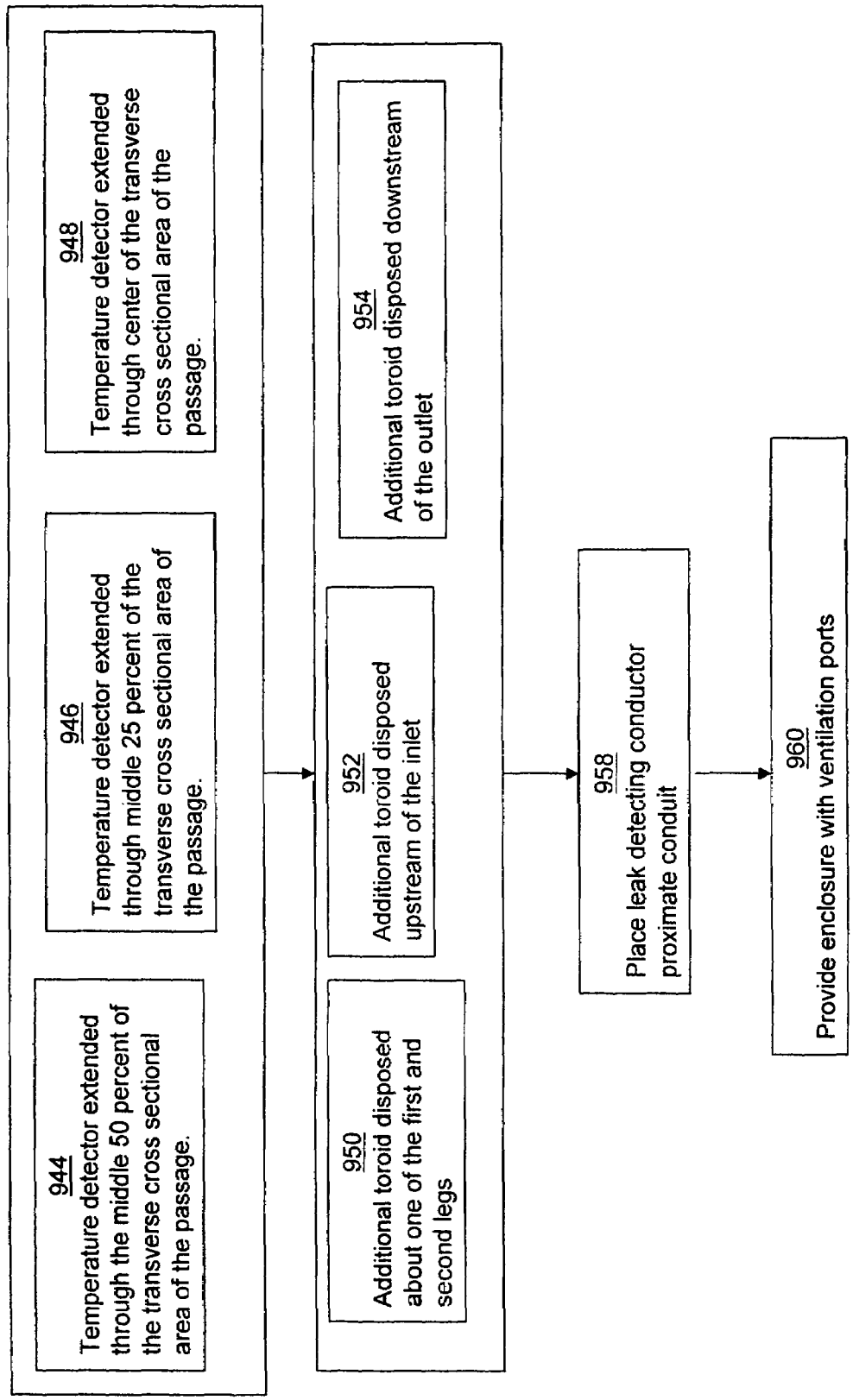

Turning now to FIGS. 18A & 18B, an exemplary method is shown and described for measuring the temperature of a process fluid in an electrodeless conductivity sensor, in accordance with an embodiment of the present invention. A non-metallic conduit is provided 930 for the flow of a process fluid in a downstream direction from an inlet to an outlet. The conduit is diverged 932 downstream of the inlet into first and second legs, and re-converged 934 upstream of the outlet to form a fluid-flow loop between the inlet and the outlet. At least one first type toroid is disposed 936 about one of the first and second legs, and at least one second type toroid is disposed 938 about one of the first and second legs, the first type and second type coils being selected from the group consisting of drive and sense coils. An electrically non-conductive holder is extended 940 into the conduit, which supports 942 a temperature detector therein so that process fluid flowing in the downstream direction passes on opposite sides of, while remaining free of physical contact with, the temperature detector.

Optionally, the temperature detector may be respectively extended 944, 946, 948, through the middle 50 percent, 25 percent, and/or center, of the transverse cross sectional area of the passage. At least one additional toroid may be disposed: 950 about one of the first and second legs; 952 upstream of the inlet; and/or 954 downstream from the outlet. A first type coil may be disposed 956 between two second type coils on each of said first and second legs.

An electrical conductor 477 may be disposed 958 in leakage-contacting relation to the conduit, the conductor having a predetermined electrical resistance, and being coupled to a port engagable by resistance measuring means for measuring resistance of the conductor to determine leakage.

An optional enclosure used to protect various system components may be provided 960 with ventilation ports.

EXAMPLES

The following illustrative examples are intended to demonstrate certain aspects of the present invention. It is to be understood that these examples should not be construed as limiting. These examples demonstrate that embodiments of this invention are effective for timely measurement of the temperature of a process fluid. In these examples, the temperature measured by the RTD successfully reached at least 90 percent of the final temperature T (or 90 percent of the temperature change ΔT) in about 1.5 minutes or less.

Example 1

Figure 20:
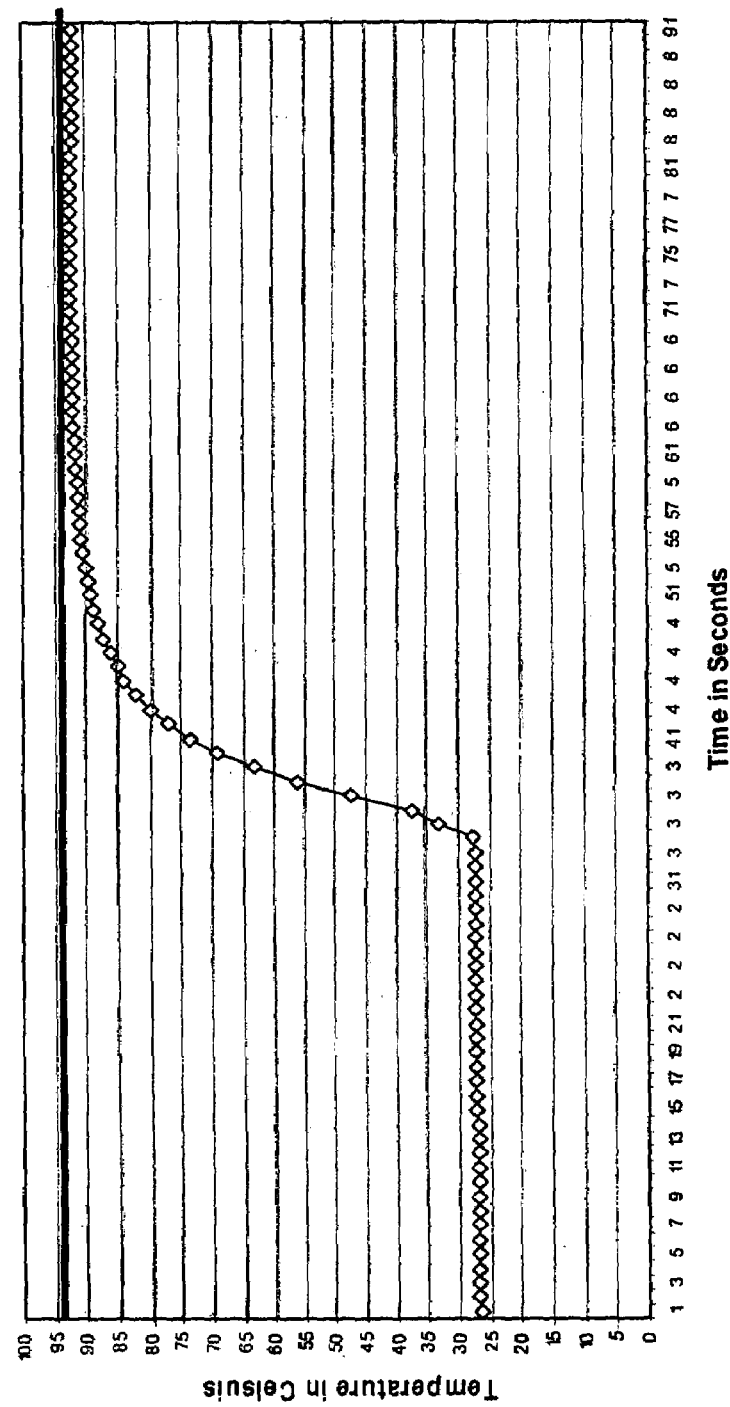
FIG. 20 is a graphical representation of temperature response testing for an exemplary device fabricated as shown and described with respect to FIG. 8.

An RTD and holder assembly as shown and described hereinabove with respect to FIG. 12, was installed into a conventional ¾ inch (outer diameter) conduit 202 fabricated from PFA, and tested to determine the temperature response. The conduit had a nominal wall thickness of 0.062 in (0.16 cm), and the holder had a minimum nominal wall thickness of 0.062 in (0.16 cm). The holder 912 was fabricated from the same material (PFA) with the same wall thickness as conduit 202. The holder 912 supported a three wire RTD with a resistance of 1000 ohms. The holder and conduit combination was placed in a fluid bath at a temperature of 94° C. The temperature detector was coupled to an analyzer, and the recorded temperature was plotted on a graph as a function of time, as shown in FIG. 20.

The recorded temperature ranged from an initial temperature of 22° C. to a final temperature T of 92.6° C. The recorded temperature reached approximately ninety percent of full temperature change ΔT in 46 seconds at 84.8° C.; and approximately 98% of the ΔT was reached at 55 seconds, when the recorded temperature was 90.8° C.

Example 2

Figure 19:
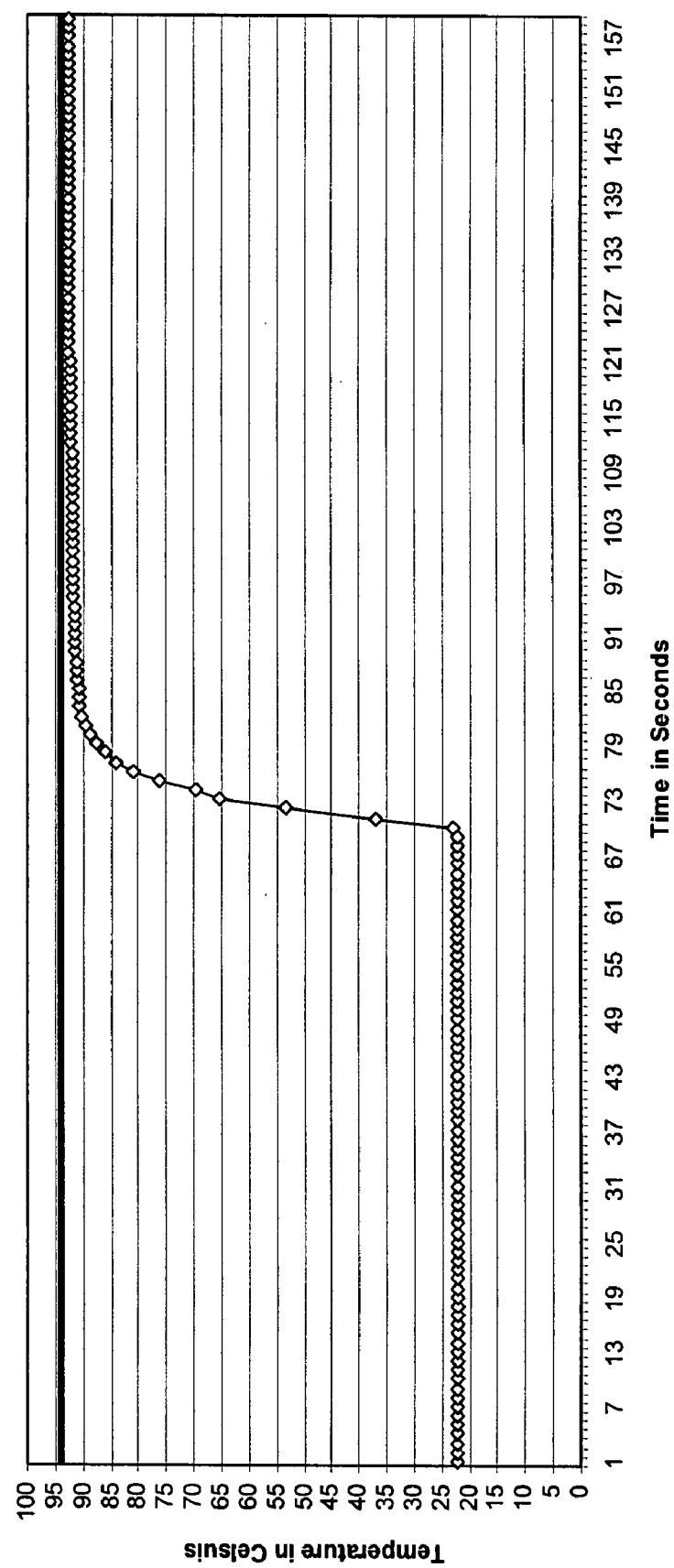
FIG. 19 is a graphical representation of temperature response testing for an exemplary device fabricated as shown and described with respect to FIG. 12.

An RTD and holder assembly as shown and described hereinabove with respect to FIG. 9, was installed into a conventional 1 inch O.D., 0.840 I.D.×2 inch conduit 202 fabricated from PFA, and tested to determine the temperature response. The conduit had a nominal wall thickness of 0.120 in (0.30 cm), and the holder had a minimum nominal wall thickness of 0.065 in (0.17 cm). The holder 902 supported a three wire temperature detector with a resistance of 1000 ohms. The prototype was placed in a fluid bath at a temperature of 93° C. The temperature detector was coupled to an analyzer, and the recorded temperature was plotted as a function of time, as shown in FIG. 19.

Ninety percent of the ΔT was recorded (85.54° C.) at 78 seconds; and approximately 98% of the ΔT was obtained at 83 seconds, at 90.5° C.

Example 3

An RTD and holder assembly as shown and described hereinabove with respect to FIGS. 15-17, was installed into a conventional ½ inch O.D. conduit 202 fabricated from PFA, and tested to determine the temperature response. The conduit had a nominal wall thickness of 0.093 in (0.24 cm), and the holder had a minimum nominal wall thickness of 0.062 in (0.16 cm). Holder 922 was fabricated from PFA, with the following dimensions as shown in FIG. 17. Dimension t2 was 0.070 in. (0.178 cm), t1 was 0.195 in. (0.495 cm), and t3 was sized and shaped to form a liquid-tight engagement with inner diameter (ID) of passage 904, of 0.390 in. (0.991 cm). Dimension a2 of the temperature detector was 0.920 in. (2.337 cm), while a1, a3 and a4 of the holder were 0.990 in. (2.515 cm), 0.245 in. (0.622 cm), and 0.090 in. (0.229 cm), respectively. This exemplary assembly provides a temperature response of at least about 90 percent of the ΔT within one minute.

In the preceding specification, the invention has been described with reference to specific exemplary embodiments thereof. It will be evident that various modifications and changes may be made thereunto without departing from the broader spirit and scope of the invention as set forth in the claims that follow. The specification and drawings are accordingly to be regarded in an illustrative rather than restrictive sense.

Although holders 902, 912, 922 and temperature detector 906 are shown and described as incorporated within the various conductivity sensors of the present invention, those skilled in the art should recognize that they may be used independently and/or in combination with nominally any type of fluid sensor, without departing from the spirit and scope of the present invention. For example, holders 902, 912, 922 and temperature detector 906 may be used in combination with various pressure detectors, conductivity sensors, pH sensors, ORP sensors, flow meters, and combinations thereof. Commercial examples of such devices include the 83 Series Vortex Flowmeters, I/A Series Pressure Transmitters, 134 Series Intelligent Displacement Transmitters, I/A Series Temperature Transmitters, 873 Series Electrochemical Analyzers, and the 871 Series conductivity, pH and ORP sensors all commercially available from Invensys Systems, Inc. of Foxboro, Mass.

What is claimed is:

1. An electrodeless conductivity sensor, comprising:
   an electrically non-conductive conduit defining a passage for the flow of a process fluid in a downstream direction, said conduit having an inlet and an outlet;
   said conduit diverging downstream of the inlet into first and second legs, said legs re-converging upstream of said outlet, to form a fluid-flow loop between said inlet and said outlet;
   at least one first toroid configured as a first type coil disposed about one of said first and second legs;
   at least one second toroid configured as a second type coil disposed about one of said first and second legs;
   said first type and second type coils selected from the group consisting of drive and sense coils;
   an electrically non-conductive elongated holder extending into said passage; and
   a temperature detector disposed within said holder, wherein process fluid flowing in the downstream direction passes on opposite sides of, while remaining free of physical contact with, said temperature detector.

2. The sensor of claim 1, wherein said temperature detector passes through the middle 50 percent of the transverse cross sectional area of the passage.

3. The sensor of claim 2, wherein said temperature detector passes through the middle 25 percent of the transverse cross sectional area of the passage.

4. The sensor of claim 3, wherein said temperature detector passes through the center of the transverse cross sectional area of the passage.

5. The sensor of claim 1, wherein said holder and said temperature detector extends into the passage substantially transversely to the downstream direction.

6. The sensor of claim 5, wherein said holder extends entirely across the passage.

7. The sensor of claim 1, wherein said holder and said temperature detector extend into the passage substantially parallel to the downstream direction.

8. The sensor of claim 7, wherein said temperature detector is disposed in a corner portion of the fluid-flow loop.

9. The sensor of claim 1, wherein said holder is fabricated from a polymeric material.

10. The sensor of claim 1, wherein said conduit is fabricated from a polymeric material.

11. The sensor of claim 1, wherein said holder is disposed within a modular adapter configured for removable engagement at any one of a plurality of spaced locations along the conduit.

12. The sensor of claim 11, wherein said holder is integral with said adapter.

13. The sensor of claim 1, further comprising a connector configured to couple said first and second toroids to an analyzer.

14. The sensor of claim 1 comprising a plurality of first type coils disposed on a same one of said first and second legs.

15. The sensor of claim 14, wherein said at least one second type coil is disposed on another one of said first and second legs.

16. The sensor of claim 1, further comprising a third toroid, wherein said first, second and third toroids are all disposed on the same one of said first and second legs.

17. The sensor of claim 16, comprising a first type coil disposed between two second type coils.

18. The sensor of claim 17, comprising a first type coil disposed between two second type coils on each of said first and second legs.

19. The sensor of claim 1, wherein coils of the same type are disposed on opposite legs from one another.

20. The sensor of claim 1, wherein coils of the same type are connected electrically in parallel with one another.

21. The sensor of claim 1, comprising at least one other toroid disposed about said conduit outside of said fluid loop.

22. The sensor of claim 21, wherein said at least one other toroid is connected electrically out of phase with sense coils disposed on said first and second legs.

23. The sensor of claim 1, comprising a fluid leak detector including an electrical conductor disposed in leakage-contacting relation to the conduit, the conductor having a predetermined electrical resistance, and a port having terminals coupled to opposite ends of the conductor, the port being couplable to resistance measuring means for measuring resistance of the conductor.

24. The sensor of claim 1, wherein a portion of said conduit is disposed within an enclosure defining an interior, said enclosure having a plurality of ports disposed for ventilating the interior.

25. A method for fabricating an apparatus for measuring the temperature of a process fluid in an electrodeless conductivity sensor, comprising:
(a) providing a non-metallic conduit defining a passage for the flow of a process fluid, the conduit having an inlet and an outlet;
(b) diverging the conduit downstream of the inlet into first and second legs;
(c) re-converging the legs upstream of the outlet to form a fluid-flow loop between the inlet and the outlet;
(d) disposing at least one first type toroid about one of the first and second legs;
(e) disposing at least one second type toroid about one of said first and second legs, wherein the first type and second type coils are selected from the group consisting of drive and sense coils;
(f) extending an electrically non-conductive holder into said passage; and
(g) disposing a temperature detector within said holder, so that process fluid flowing in the downstream direction passes on opposite sides of, while remaining free of physical contact with, the temperature detector.

26. The method of claim 25, comprising extending the temperature detector through the middle 50 percent of the transverse cross sectional area of the passage.

27. The method of claim 26, comprising extending the temperature detector through the middle 25 percent of the transverse cross sectional area of the passage.

28. The method of claim 27, comprising extending the temperature detector through the center of the transverse cross sectional area of the passage.

29. The method of claim 25, further comprising disposing at least one additional toroid about one of the first and second legs.

30. The method of claim 25, further comprising disposing at least one additional toroid about the conduit upstream of the inlet.

31. The method of claim 25, further comprising disposing at least one additional toroid about the conduit downstream from the outlet.

32. The method of claim 25, comprising disposing a first type coil between two second type coils on each of said first and second legs.

33. The method of claim 25, comprising disposing an electrical conductor in leakage-contacting relation to the conduit, the conductor having a predetermined electrical resistance, and coupling a port to opposite ends of the conductor, the port being engagable by resistance measuring means for measuring resistance of the conductor to determine leakage.

34. The method of claim 25, comprising disposing a portion of the conduit within an enclosure defining an interior, providing the enclosure with a plurality of ports, and ventilating the interior through the ports.

* * * * *